(12) United States Patent
Torii et al.

(10) Patent No.: US 6,805,442 B2
(45) Date of Patent: Oct. 19, 2004

(54) APPARATUS FOR ANALYZING A SECTIONAL IMAGE OF AN ANTERIOR EYE SEGMENT AND A PROGRAM FOR THE SAME

(75) Inventors: Miwako Torii, Toyohashi (JP); Setsuo Saito, Aichi-gun (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/188,793

(22) Filed: Jul. 5, 2002

(65) Prior Publication Data

US 2003/0012412 A1 Jan. 16, 2003

(30) Foreign Application Priority Data

Jul. 11, 2001 (JP) ........................................ 2001-211359

(51) Int. Cl.⁷ .............................. A61B 3/10; A61B 3/00
(52) U.S. Cl. ...................................... 351/214; 351/246
(58) Field of Search ................................ 351/200, 205, 351/206, 214, 221, 246; 600/558; 128/898

(56) References Cited

U.S. PATENT DOCUMENTS

| 5,347,331 A | 9/1994 | Isogai et al. |
| 5,864,382 A | 1/1999 | Soya et al. |

FOREIGN PATENT DOCUMENTS

| EP | 0811352 A2 | * 12/1997 | ................. 351/206 |
| EP | 0 933 060 A1 | 8/1999 | |

OTHER PUBLICATIONS

Hayashi, Ken, Hayashi, Hideyuki, Nakao, Fuminori and Hayashi, Fumihiko, "Reproducibility of posterior capsule opacification measurement using Scheimpflug videophotography," J Cataract Refract Surg, vol. 24, Dec. 1998, pp. 1632–1635.

Onishi, Takeo and Yaguchi, Shigeo, "Modified EAS1000 algorism for measuring posterior capsular opacification," Jpn J Clin Ophthalmol, 53 (3): 311–315, 1999.

* cited by examiner

Primary Examiner—Brian L. Casler
Assistant Examiner—John R Sanders
(74) Attorney, Agent, or Firm—Oliff & Berridge, PLC

(57) ABSTRACT

The present invention intends to provide an apparatus for analyzing a sectional image of an anterior eye segment and a program for the same which reduce a burden on an examiner, and to provide a more reliable, reproducible result. The apparatus for analyzing a sectional image of an anterior eye segment which is light-sectioned by slit light and photographed comprises a defining device for defining a target opacity part in the sectional image based on a density distribution being between a cornea and a fundus and being in a first direction perpendicular to an optical axis of an eye to be examined, a determining device for determining an area to be analyzed based on the defined opacity part, and an analyzing device for analyzing an opacity condition base on the density distribution in the determined area.

4 Claims, 3 Drawing Sheets

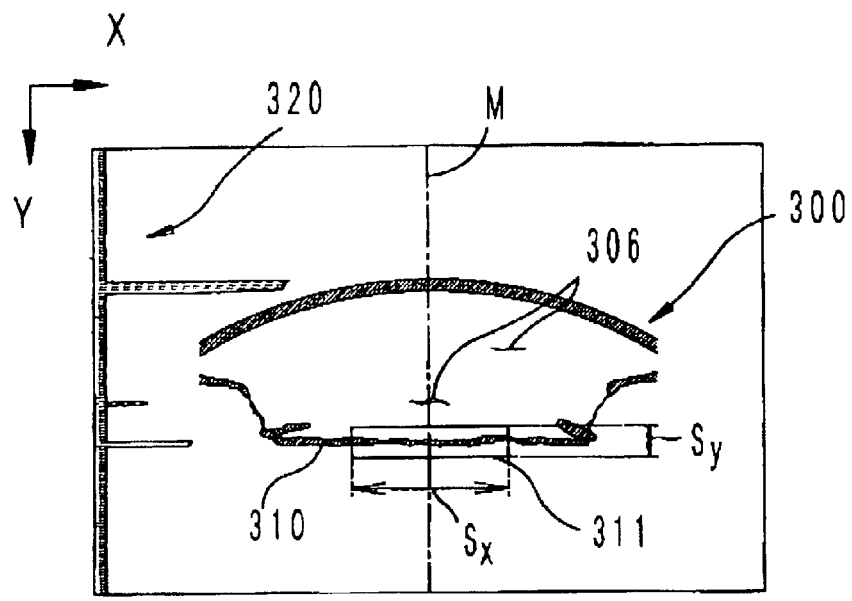
FIG. 3
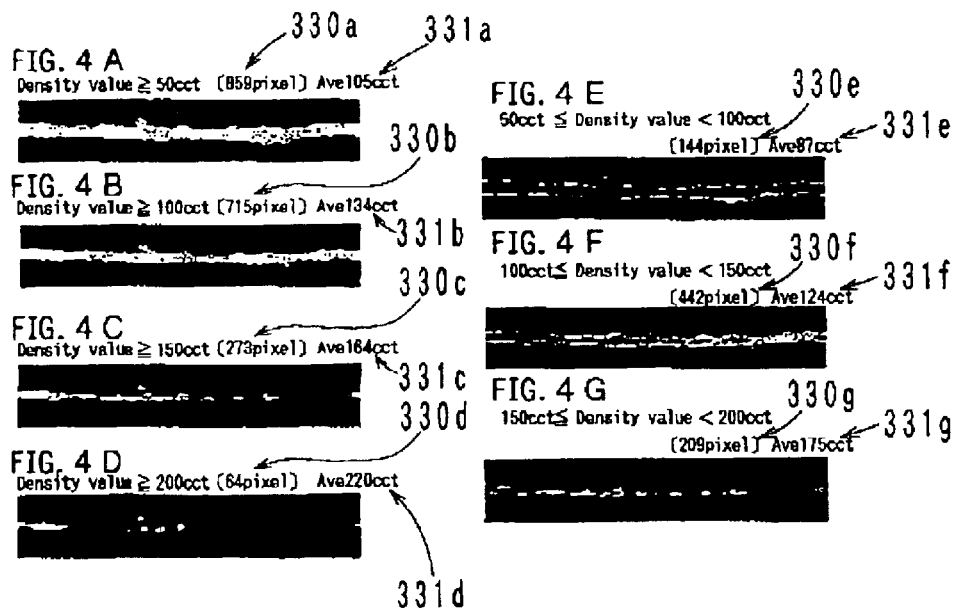

APPARATUS FOR ANALYZING A SECTIONAL IMAGE OF AN ANTERIOR EYE SEGMENT AND A PROGRAM FOR THE SAME This application claims priority from Japanese Patent Application No. 2001-211359 filed Jul. 11, 2001, the disclosure of which is incorporated herein by reference thereto.

BACKGROUND OF THE INVENTION

1. Field of the Invention

The present invention relates to an apparatus for analyzing a sectional image of an anterior eye segment and a program for the same.

2. Description of Related Art

Implantation of an intraocular lens after removing a crystalline lens in cataract surgery may cause posterior capsule opacity which may develop a so-called secondary cataract. Methods for evaluating posterior capsule opacity in an eye in which an intraocular lens has been implanted include analyzing a sectional image of an anterior eye segment light-sectioned by slit light and photographed under the Scheimpflug's rule. Through this method, it is possible to obtain a clear image from a cornea to a posterior capsule in one shooting, thereby facilitating quantification analysis through the use of this photographed image.

Through conventional quantification analysis of a posterior capsule opacity part, however, an examiner mainly checks a sectional image of an anterior eye segment and a bar graph showing a density distribution on an axis, and he manually sets an area to be analyzed. Due to the manual setting, the examiner tends to subjectively define the posterior capsule opacity part. As a result, reproducibility among examiners tends to be low. Also, an examiner needs to move the analytical axis every time he intends to check a density distribution of areas other than the analytical axis, and the checking is a cumbersome task to him.

SUMMARY OF THE INVENTION

The present invention has been made in view of the above circumstances and has an object to overcome the above problems and to provide an apparatus for analyzing a sectional image of an anterior eye segment and a program for the same which reduce a burden on an examiner, and to provide a more reliable, reproducible result. In addition, the present apparatus and program enables an examiner to grasp an opacity condition more quantitatively as well as to easily grasp it visually.

To achieve the objects and in accordance with the purpose of the present invention, as embodied and broadly described herein, an apparatus for analyzing a sectional image of an anterior eye segment which is light-sectioned by slit light and photographed comprises defining means for defining a target opacity part in the sectional image based on a density distribution being between a cornea and a fundus and being in a first direction perpendicular to an optical axis of an eye to be examined, determining means for determining an area to be analyzed based on the defined opacity part, and analyzing means for analyzing an opacity condition base on the density distribution in the determined area.

In another aspect of the present invention, an apparatus for analyzing a sectional image of an anterior eye segment which is light-sectioned by slit light and photographed comprises determining means for determining in a sectional image an area to be analyzed including a target opacity part, extracting means for dividing a density distribution in the determined area into plural density ranges to extract each of the divided density distributions, and display means for graphically displaying each of the extracted density distributions.

Yet, in another aspect of the present invention, a program for analyzing a sectional image of an anterior eye segment which is light-sectioned by slit light and photographed activates a computer as defining means for defining a target opacity part in the sectional image based on a density distribution being between a cornea and a fundus and being in a first direction perpendicular to an optical axis of an eye to be examined, determining means for determining an area to be analyzed based on the defined opacity part, and analyzing means for analyzing an opacity condition based on the density distribution in the determined area.

Yet, in another aspect of the present invention, a program for analyzing a sectional image of an anterior eye segment which is light-sectioned by slit light and photographed activates a computer as determining means for determining in a sectional image an area to be analyzed including a target opacity part, extracting means for dividing a density distribution in the determined area into plural density ranges to extract each of the divided density distributions, and display control means for graphically displaying each of the extracted density distributions on a display.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 3 is a view illustrating analysis of posterior capsule opacity; and

FIGS. 4A to 4G are views showing display examples of analytic results.

DETAILED DESCRIPTION OF THE PREFERRED EMBODIMENTS

Figure 1:
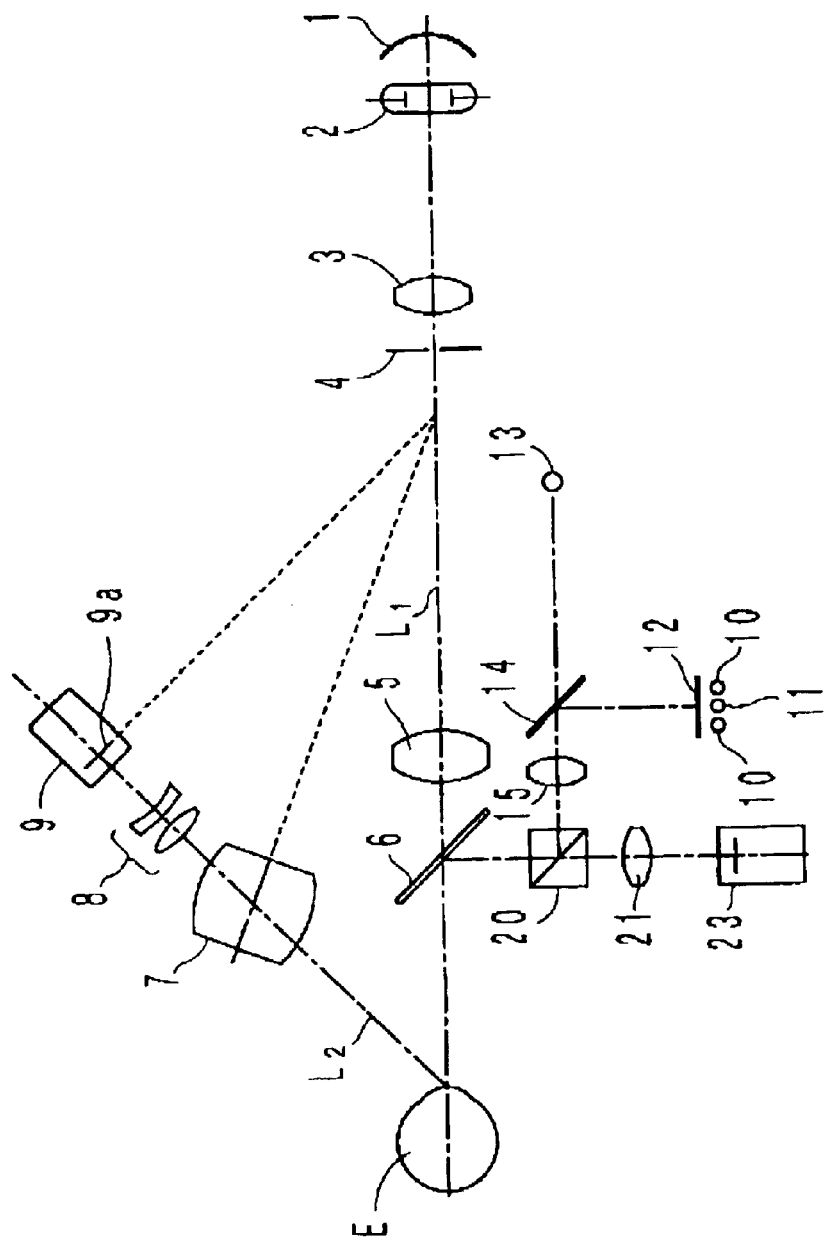
FIG. 1 is a view showing a schematic configuration of an optical system for photographing an anterior eye segment.

A detailed description of one preferred embodiment of an apparatus for analyzing a sectional image of an anterior eye segment and a program for the same embodying the present invention will now be given referring to the accompanying drawings. FIG. 1 is a view showing a schematic configuration of an optical system for photographing an anterior eye segment. The optical system for photographing the anterior eye segment is roughly constituted of a slit-light projecting optical system, a slit-section photographing optical system, an alignment-target projecting optical system, a fixation-target presenting optical system, and a photographing optical system for a front of the anterior eye segment.

Slit-light Projecting Optical System

Reference numeral 1 indicates a reflecting mirror, 2 is a flash lamp for photographing, 3 is a condenser lens, 4 is a slit-aperture diaphragm, 5 is a projecting lens, and 6 is a dichroic mirror disposed slantingly on an optical axis L1 of the slit-light projecting optical system. The dichroic mirror 6 has a property of transmitting most of visible light but reflecting part of visible light and all of infrared light (near-infrared light).

Visible white light emitted from the lamp 2 converges by the lens 3 to illuminate the diaphragm 4. The light limited in narrow slit shape by the diaphragm 4 passes through the lens 5 and the dichroic mirror 6 to be projected onto an eye to be examined E. Optic media (a cornea, an anterior chamber, a crystalline lens, and the like) of an anterior segment of the eye E are illuminated and light-sectioned by the visible white light.

Slit-section Photographing Optical System

Reference numeral 7 is a photographing lens, 8 is an anamorphic lens for correcting a distortion of an image, and 9 is a CCD camera for photographing a slit-sectional image. An optical axis L2 of the slit-section photographing optical system is placed so as to incline toward the optical axis L1 of the slit-light projecting optical system at an angle of 45 degrees. The lens 7 is arranged to incline toward the optical axis L2, thereby satisfying the Scheimpflug's rule. That is, the lens 7 is arranged so that an extension of a light-sectioned plane of the anterior segment of the eye E and an extension of a photographing plane 9a of the camera 9 intersect on an extension of a main plane of the lens 7. This optical arrangement allows the sectional image formed on the photographing plane 9a of the camera 9 to have a focal depth at which the approximately entire image is in focus.

Alignment-target Projecting Optical System

Reference numeral 13 indicates a near-infrared light source for alignment, 14 is a dichroic mirror having a property of reflecting most of infrared light (near-infrared light) but transmitting part of infrared light, and reflecting all of visible light, and 15 is a projecting lens. Part of near-infrared light emitted from the light source 13 is transmitted through the dichroic mirror 14, is made to be a parallel light bundle by the projecting lens 15, and is partially reflected by a half mirror 20. Then, this light is reflected by the dichroic mirror 6 and proceeds along the optical axis L1 toward the eye E, thereby forming an image of the light source 13 inside the eye E at a distance of half a radius of corneal curvature from a corneal vertex.

Fixation-target Presenting Optical System

Reference numeral 10s indicate light sources for eye fixation. In the present embodiment, each of right and left eyes is provided with one light source 10, and images are photographed by coinciding a geometric axis (an optical axis) of the eye E with the optical axis L2, so that an image photographed from a nose side and that from an ear side are mirror images of each other. A light source 11 emits near-infrared light for photographing a retroillumination image. A target plate 12 includes pinholes at positions corresponding to the two light sources 10s and the light source 11. Visible light emitted from the light sources 10 lit individually illuminates the target plate 12. The light having passed through the target plate 12 is reflected by the dichroic mirror 14, and is projected onto the eye E via the lens 15, the half mirror 20, and the dichroic mirror 6.

Photographing Optical System for a Front of an Anterior Eye Segment

Reference numeral 21 indicates a photographing lens, and 23 is a CCD camera for observing a front of the anterior eye segment having a sensitivity to the infrared region (near-infrared region). The alignment light projected by the alignment-target projecting optical system and partially reflected by the cornea is reflected by the dichroic mirror 6. Then, it passes through the half mirror 20 and the photographing lens 21 to be photographed by the camera 23. In addition, an image of the anterior segment of the eye E illuminated by a light source (not illustrated and emitting near-infrared light) for illuminating the anterior eye segment is also photographed by the camera 23 via the above-described optical path.

Figure 2:
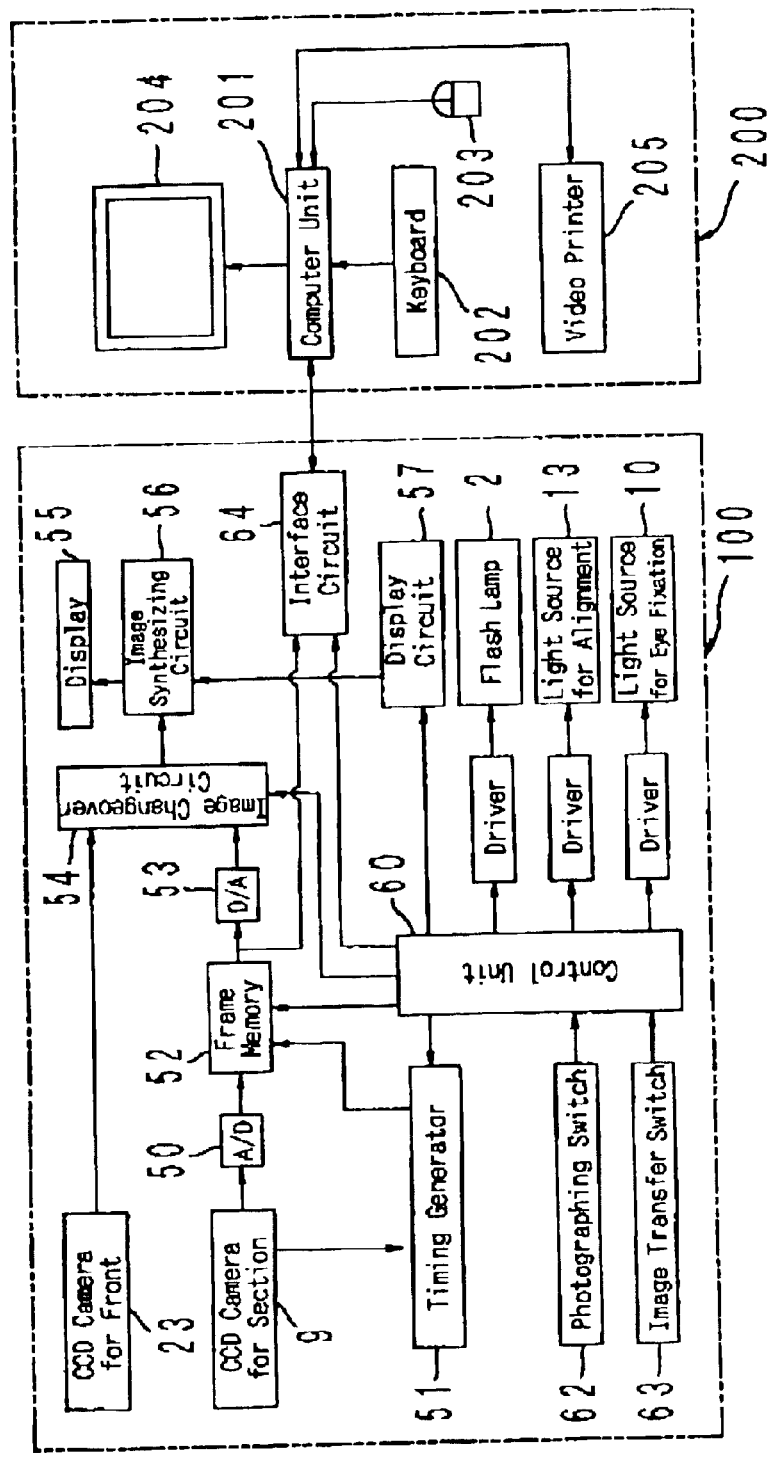
FIG. 2 is a block schematic diagram of a control system in a photographing unit for the anterior eye segment and an image-analyzing unit.

FIG. 2 is a block schematic diagram of a control system in a photographing unit for the anterior eye segment and an image-analyzing unit.

Photographing Unit for the Anterior Eye Segment

The photographing optical system for the anterior eye segment described above is disposed in a photographing unit 100 for the anterior eye segment. A signal outputted from the camera 9 is digitized by an A/D converting circuit 50 and is inputted to a frame memory 52 being synchronized with a signal given from a timing generator 51. The image signal stored in the frame memory 52 is converted to a video signal by a D/A converting circuit 53 to be sent to an image changeover circuit 54. The image changeover circuit 54 receives a command signal from a control unit 60 and changes an image displayed on a display 55 by shifting (switching) between the images photographed by the cameras 23 and 9. An image synthesizing circuit 56 synthesizes a display of various types of information (characters, symbols, and so on) created by a display circuit 57 with the images photographed by the cameras 9 and 23 to display the synthesized image and information on the display 55.

According to a signal (command signal) inputted from an image transfer switch 63, the sectional image of the anterior eye segment temporarily stored in the frame memory 52 is transferred to an image-analyzing unit 200 via an interface circuit 64.

Image-analyzing Unit

A computer unit 201 performs image processing on the sectional image given from the photographing unit 100 and analyzes it, and it includes a memory for storing the image and an analyzing program. The computer unit 201 connects to a keyboard 202 and a mouse 203 for giving an instruction. A color display 204 displays the sectional image given from the photographing unit 100 and an analytical result. The display 204 and a video printer 205 are controlled by the computer unit 201.

Operations of the apparatus having the above-described construction will be described. After placing the eye E at a predetermined position, an examiner makes the eye E of an examinee fixed on the target plate 12. The frontal image of the eye E photographed by the camera 23 is displayed on the display 55 via the image changeover circuit 54. The examiner operates a joystick and the like (not illustrated) to vertically and horizontally move the photographing unit 100 for aligning it with the eye E, so that the alignment-target image (the image of the light source 13) displayed on the display 55 may have a predetermined relationship with a reticle mark formed electrically (it may be formed optically) on the display 55. By carrying out this operation, the optical axis of the photographing optical system for the anterior eye segment and the optical axis of the eye E can be aligned. Further, the examiner performs alignment for a working distance by moving the photographing unit 100 back and forth to achieve the smallest and clearest alignment-target image.

Completing the alignment by performing the above-described operations, the examiner presses a photographing switch 62 to light the lamp 2. Then, the camera 9 photographs the sectional image of the anterior eye segment light-sectioned by the slit light. While the photographed image is stored in the frame memory 52, it is displayed on the display 55. The sectional image stored in the frame memory 52 is transferred to the image-analyzing unit 200 by turning the switch 63 on.

Next, the image-analyzing unit 200 (computer unit 201) detects an opacity part in intraocular tissue (in a posterior capsule in this embodiment) from the photographed sectional image and analyzes an opacity condition. The sectional image transferred from the photographing unit 100 is inputted to a frame memory included in the computer unit 201. Also, the sectional image inputted in the frame memory is displayed on the color display 209. The examiner uses the mouse 203 to input a command signal for analysis. Here, a description will be given to the case of selecting a mode for analyzing the posterior capsule opacity in an eye in which an intraocular lens has been implanted. The image-analyzing unit 200 analyzes in accordance with the analyzing program of the selected mode. Analyzing steps will be described hereinafter.

The photographed sectional image is based on light scattering from each part of the anterior eye segment light-sectioned by the slit light, and opacity can be detected based on a density of the scattering light. First, with respect to the sectional image stored in the frame memory, the direction of the optical axis of the eye E is specified as a direction of a Y axis, and a direction perpendicular to the Y axis is specified as a direction of an X axis. As shown in FIG. 3, an upper-left corner on the frame memory is assigned as an origin point of an XY coordinate system. Since the sectional image is stored in the frame memory as a digitized image, the density of the sectional image can be obtained in numerical form. Density values are expressed in 256 levels ranging from 0 to 255. Higher values indicate higher density. In FIG. 3, reference numeral 300 indicates the photographed sectional image of the anterior eye segment.

Determining an Analytical Axis

The sectional image 300 of the anterior eye segment is scanned in the Y-axis direction to obtain density changes. Then, first, a position of a corneal frontal surface is detected. The position of the corneal part can be detected by identifying a region where a density changes drastically (which can be identified by a density change with respect to a specified number of pixels in the Y-axis direction) and where the density shows the highest density. The position of the corneal frontal surface, for example, can be determined on a position at half a distance between a density peak and a density bottom on the increasing side of the highest density. A position of a corneal rear surface can be determined in the same manner on the decreasing side of the highest density. This is repeated at all or part of the X coordinate to obtain the coordinates of the corneal frontal surface. Next, three or more positions arbitrarily spaced on the coordinates of the corneal frontal surface are pointed (the more points are taken, the more accurate result is obtained), and a curvature center of the corneal frontal surface is obtained by circularly approximating these positions. On a curve of the corneal frontal surface circularly approximated, a corneal vertex is determined at a point nearest to the origin point in the Y-axis direction. Then, a line passing through the corneal vertex and the curvature center of the corneal frontal surface is determined as an analytical axis M (See FIG. 3).

Determining an Area to be Analyzed

With reference to the analytical axis M, a section of a predetermined number of pixels in positive and negative directions of the X axis is determined as an analytical range in the X-axis direction. For example, considering a region in which analysis of the posterior capsule opacity is necessary, a section of pixels corresponding to 3 mm on the eye E with the analytical axis M at the center therein is determined as an analytical range Sx.

Next, a description will be given to how to determined an analytical range in the Y-axis direction. It can be basically said that an anterior chamber, an intraocular lens implanted in an eye, and a vitreous body have almost no factor for light scattering unless an examinee has particular diseases. In addition, after implantation of the intraocular lens, opacity usually develops due to the remainder of a lens capsule, a cortex lentis, and the like which show high densities in the sectional image. Accordingly, among the density changes obtained by scanning in the Y-axis direction, a region where a density change shows the highest density, which can be found between the position of the corneal rear surface and a fundus, can be detected, and it can be identified as the posterior capsule opacity part. However, some intraocular lenses might induce halation and/or a ghost causing light to be scattered in an anterior chamber. Therefore, the posterior capsule opacity part may not be detected by simply taking the density changes only in the Y-axis direction into account. In FIG. 3, for example, reference numeral 306 indicates a light-scattering part 306.

Then, the posterior capsule opacity part is distinguished from the light-scattering part 306 in the anterior chamber based on extensiveness of a high density region in the X-axis direction between the cornea and the fundus. For identifying the posterior capsule opacity part, first, the density changes in the Y-axis direction are obtained for the analytical range Sx in the X-axis direction. Then, the regions showing high density values between the cornea and the fundus is successively examined. A region which approximately linearly extends to the greatest extent (most widely) in the X-axis direction is defined as the posterior capsule opacity part. That is, in the example of FIG. 3, a light-scattering part 310 is the region which linearly extends to the greatest extent in the X-axis direction, and the light-scattering part 306 linearly extends in the X-axis direction less extensively than the light-scattering part 310. Accordingly, the light-scattering part 310 is defined as the posterior capsule opacity part 310.

Once the posterior capsule opacity part 310 is identified, an analytical range Sy in the Y-axis direction can be determined with reference to the posterior capsule opacity part 310 as a center of the analytical range Sy For example, considering a width of the posterior capsule opacity part 310 expanding in the Y-axis direction, the analytical range Sy is determined at a section of pixels corresponding to 0.25 mm on the eye E. Then, the analytical range Sy is determined so that the posterior capsule opacity part 310 may be uniformly placed approximately at a center of the analytical range Sy. Besides, an area confined by the analytical ranges Sx and Sy is determined as an area to be analyzed 311.

It should be noted that each width of Sx and Sy of the area 311 can be preset at an arbitrary value in a setting form for an analyzing parameter. When the area 311 determined automatically is not appropriate, or when the opacity part 310 cannot be defined due to nonuniform or noncontinuous densities of the light-scattering parts, it is also possible to manually determine the area 311 in a conventional way with the mouse 203 and the like. In FIG. 3, on the left of the screen, a bar graph 320 is shown to present density changes on the analytical axis M. Therefore, the examiner can define the opacity part 310 based on the density changes in the bar graph 320. Further, the examiner can obtain the bar graph 320 showing density changes from a line other than the analytical axis M. He can use the mouse 203 to arbitrarily move the line on the sectional image 300.

Further, the area 311 may be also determined in the following way. A black level of the photographed sectional image is set at zero computer compatible tapes (cct), and a part with a certain threshold level (e.g. 50 cct) or a greater threshold is judged as the light-scattering part. The part approximately linearly extending in the X-axis direction to the greatest extent (most widely) is defined as the posterior opacity part 310.

Analysis of the Opacity Condition

A density distribution of the area 311 determined as described above is divided into plural density ranges, and pixels are extracted therefrom to be graphically displayed on the display 204. FIGS. 4A to 4G are display examples, and the sections of the pixels are extracted and enlargedly displayed. FIG. 4A shows the section with the density value of 50 cct or greater, FIG. 4B shows the section with the density value of 100 cct or greater, FIG. 4C shows the section with the density value of 150 cct or greater, and FIG. 4D shows the section with the density value of 200 cct or greater. Further, FIG. 4E shows the section with the density value of 50 cct or greater and smaller than 100 cct, FIG. 4F shows the section with the density value of 100 cct or greater and smaller than 150 cct, and FIG. 4G shows the section with the density value of 150 cct or greater and smaller than 200 cct. A graphic display of the density distribution of a certain density range at plural levels facilitates visual understanding of the opacity condition. Further, in the density ranges of FIGS. 4A to 4G, numbers of pixels 330a to 330g in the area 311 and average density values 331a to 331g are individually displayed in numerical form as the analytical results. This allows the examiner to quantitatively evaluate the condition of the opacity.

In addition, the analytical results may be shown by combining FIGS. 4D, 4E, 4F, and 4G and by mapping and displaying each of the density ranges in color.

The above description has been given to an example of analysis of posterior capsule opacity in an eye in which an intraocular lens has been implanted. This invention may be also applied to analysis of opacity in tissue of frontal or rear surfaces of a cortex lentis.

As described so far, the present invention reduces a burden on an examiner and provides a more reliable, reproducible analytical result. Further, the present invention gives a way to grasp a condition of opacity more quantitatively while it enables the examiner to easily grasp the condition visually.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for analyzing a sectional image of an anterior eye segment of an eye which is light-sectioned by slit light and photographed, the apparatus comprising:

defining means, in case that a direction of an optical axis of the eye being specified as a direction of a Y-axis, a direction perpendicular to the Y-axis direction being specified as a direction of an X-axis, and an XY coordinate system being assigned to the sectional image, for defining an opacity part of a posterior capsule of the eye based on extensiveness of a light-scattering part in the X-axis direction, the light-scattering part being between a rear surface of a cornea of the eye defined based on a density change of the sectional image and a fundus of the eye and having a density sharply changed in the Y-axis direction in an analytical range in the X-axis direction;

determining means for determining an area to be analyzed by determining an analytical range in the Y-axis direction based on the defined opacity part of the posterior capsule;

analyzing means for analyzing an opacity condition of the opacity part of the posterior capsule based on a density distribution in the determined area; and display means for displaying a result of analysis by the analyzing means.

2. The apparatus according to claim 1, wherein the analyzing means further comprising extracting means for dividing the density distribution in the determined area into plural density ranges to extract each of the divided density distributions, and the display means graphically displays each of the extracted density distributions.

3. A program embodied on a computer-readable medium for analyzing a sectional image of an anterior eye segment of an eye which is light-sectioned by slit light and photographed, the program activating a computer as:

defining means, in case that a direction of an optical axis of the eye being specified as a direction of a Y-axis, a direction perpendicular to the Y-axis direction being specified as a direction of an X-axis, and an XY coordinate system being assigned to the sectional image, for defining opacity part of a posterior capsule of the eye based on extensiveness of a light-scattering part in the X-axis direction, the light-scattering part being between a rear surface of a cornea of the eye defined based on a density change of the sectional image and a fundus of the eye and having a density sharply changed in the Y-axis direction in an analytical range in the X-axis direction;

determining means for determining an area to be analyzed by determining an analytical range in the Y-axis direction based on the defined opacity part of the posterior capsule;

analyzing means for analyzing an opacity condition of the opacity part of the posterior capsule based on a density distribution in the determined area; and display control means for displaying a result of analysis by the analyzing means.

4. The program according to claim 3, wherein the analyzing means further comprising extracting means for dividing the density distribution in the determined area into plural density ranges to extract each of the divided density distributions, and the display control means graphically displays each of the extracted density distributions on a display.

* * * * *